(12) United States Patent
Miller

(10) Patent No.: US 7,706,876 B2
(45) Date of Patent: Apr. 27, 2010

(54) INTERNAL DEFIBRILLATOR OPERABLE WITH ONE HAND

(75) Inventor: James L. Miller, Westford, MA (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 497 days.

(21) Appl. No.: 10/597,394

(22) PCT Filed: Jan. 24, 2005

(86) PCT No.: PCT/IB2005/050277

§ 371 (c)(1),
(2), (4) Date: Jul. 24, 2006

(87) PCT Pub. No.: WO2005/072823

PCT Pub. Date: Aug. 11, 2005

(65) Prior Publication Data

US 2009/0192559 A1     Jul. 30, 2009

Related U.S. Application Data

(60) Provisional application No. 60/540,998, filed on Feb. 2, 2004.

(51) Int. Cl.
*A61N 1/39* (2006.01)
(52) U.S. Cl. ............... 607/5; 607/116; 607/119; 607/129; 128/800
(58) Field of Classification Search .......... 607/1–8, 607/28, 12, 10; 600/509, 518–519; 606/41, 606/51, 52
See application file for complete search history.

(56) References Cited

U.S. PATENT DOCUMENTS

| 4,273,114 A | | 6/1981 | Barkalow et al. |
| 5,213,113 A | * | 5/1993 | Hlinsky ................ 607/152 |
| 5,540,724 A | * | 7/1996 | Cox ........................ 607/8 |
| 6,246,907 B1 | * | 6/2001 | Lin et al. ................. 607/5 |
| 6,580,945 B2 | * | 6/2003 | Mulhauser et al. ......... 607/5 |
| 2002/0058934 A1 | * | 5/2002 | Wang et al. .............. 606/41 |
| 2002/0138103 A1 | | 9/2002 | Mulhauser et al. |
| 2002/0143278 A1 | | 10/2002 | Bystrom et al. |
| 2003/0191501 A1 | * | 10/2003 | Miller et al. .............. 607/5 |
| 2003/0233127 A1 | | 12/2003 | Ryczek |

FOREIGN PATENT DOCUMENTS

WO     0158522 A     8/2001

* cited by examiner

*Primary Examiner*—Carl H Layno
*Assistant Examiner*—Paula J Stice
(74) *Attorney, Agent, or Firm*—W. Brinton Yorks, Jr.

(57) ABSTRACT

A single-handle cordless internal defibrillator includes a pair of paddles, and a pair of electrodes that are respectively connected to a first-end portion of the pair of paddles. The pair of paddles has a second-end portion in communication with a single-handle, with a least one paddle of the pair of paddles being pivotable about a pivot arranged between the one paddle and the single-handle. A regulator arm in communication with the pivot adjusts the pivot of at least one paddle about the pivot so that the distance between the electrodes is variable by moving the regulator arm, and defibrillator circuitry is arranged within the single-handle. A dual-handle structure also provides tangle-free and clutter-free applications as the defibrillator circuitry is self-contained in the handle/handles or paddles of the defibrillator, eliminating the need for long cables which obstruct and can contaminate an operating room.

5 Claims, 2 Drawing Sheets

INTERNAL DEFIBRILLATOR OPERABLE WITH ONE HAND

CROSS REFERENCE TO RELATED APPLICATION

This application claims the benefit of U.S. provisional application Ser. No. 60/540,998 filed Feb. 2, 2004, which is incorporated herein.

BACKGROUND OF THE INVENTION

The present invention relates to medical devices that are used to provide emergency cardiac care for conditions during open-heart surgery. More particularly, the present invention relates to internal defibrillators and their means for delivering electrical energy to a patient during surgery.

There are many different types of defibrillators on the market today, but they all can be classified in one of two categories; external and internal defibrillators. External defibrillators, which include types requiring little sophistication from the user, such as Automatic External Defibrillators, are beginning to be located in public places such as theatres and shopping centers in order to save lives. External defibrillators are applied to the patient topically, i.e., through the skin, whereby a pulse applied to the patient travels through the skin, the thorax tissue, and then to the heart.

However, internal defibrillators are designed for use particularly during open-heart surgery. During such surgery, it is a common practice that the heart is prevented from beating (with the person being hooked up to a life-support heart-bypass machine) so that the surgeons can operate on the heart. After the surgeons have repaired/removed whatever was causing the problem, an internal defibrillator is applied directly onto the heart to jump-start its beating. This defibrillation is performed by the surgeon using two special internal-defibrillation-paddle electrodes, wherein the surgeon inserts the internal paddle electrodes into the patient's open chest to restart the heart. The electrode paddles must be sterile to avoid contaminating/infecting the heart. Normally, the surgeon holds one paddle in each hand and places the two electrodes against opposite sides of the heart so that an electrical discharge is passed from one electrode through the heart to the second electrode.

The electrical discharge is currently supplied from a large general-purpose defibrillator. Since the defibrillator is not sterile, it must be placed outside the sterile operating field and located some distance from the patient. The paddles are connected to the defibrillator by long cables draped from the defibrillator to the patient's open chest. One cable is connected to each paddle electrode.

The conventionally-used cables and electrodes suffer from at least the following problems. Two people are required to set up the internal defibrillator for use during an operation. First, a "sterile" person is required to prepare the sterile electrode paddles in a sterile field of the operating room. However, the location of the defibrillator is outside the sterile field. A second "non-sterile" person is required to receive the cable connector from the "sterile" person and connect it to the defibrillator.

The long cables draped from the defibrillator to the patient's open chest need to be large and bulky to be able to deliver a high voltage shock to the patient. Shocks as high as 1,000 volts and exceeding 50 amps at discharge require the cable to be large, hard to handle, and prone to tangle. The cables are also bulky in order to protect the user from shock, as defibrillators of this type having electrical discharges as high 1,000 volts require the cable insulation to be relatively thick, thus limiting the cable flexibility.

The consequences of having such big, bulky cables fed from across the room from a non-sterile area are numerous. These cables can interfere with the placement of the electrode paddles, and are a common failure point. In addition, the cables invariably get in the way of the surgeon during an operation, impeding the entire operating room. Moreover, the cables themselves, as well as the cable connections, are often common points of failure in the system.

The internal paddles/cables of a conventional defibrillator are not interchangeable with different defibrillators, meaning that the hospitals must keep spares for each machine that requires a lengthy replacement process by qualified personnel. Finally, as there are two separately-held electrode paddles (one in each hand) there is an operator safety issue looming because there is always a possibility that the operator may inadvertently shock him/herself with one of the paddles.

Thus, a need exists for an improvement in the defibrillator's delivery of electrical shock to the patient.

The present invention overcomes many of the aforementioned problems of conventional internal defibrillators. According to the present invention an optimized cordless defibrillator is built into the handles of the paddle electrodes, thereby eliminating all the problems and limitations of using thick bulky cables. Moreover, this arrangement eliminates the need for the general-purpose defibrillator to be placed in an area outside the sterile field. No longer is it necessary to have two people set up the defibrillator and cables for use.

In the present application, the term "paddle" is used throughout. For purposes of this application, it is to be understood by an artisan that the term paddle refers to the handle, shaft, and electrode. Additionally, an internal defibrillator comprises a paddle along with the electronics necessary to administer a therapeutic shock being arranged within one or more paddles.

The cordless defibrillator eliminates the heavy, inflexible cables of conventional internal-defibrillator systems that get in the way of the doctors and nurses, and/or get tangled up and require untangling when time could be critical. A common point of failure is also eliminated, and the possibility of contamination is decreased as the entire unit can be located in the sterile field.

According to one aspect of the present invention, the two paddles can be controlled by a single-handle that is held and used with only one hand, increasing the potential accuracy and safety of the invention as compared with holding each paddle by a separate handle, as the single-handle does not require separate placement in the patient's chest to administer the shock. A predetermined distance between the electrodes can be adjusted by a regulator arm prior to inserting the paddles into the patient's chest, and then the paddles can be placed more accurately in the patient to administer the shock across the desired portions of the heart by the operator holding a single handle, rather than two independent handles.

According to another aspect of the present invention, some or all of the internal defibrillator components may be disposable, thus eliminating the need for cleaning and sterilizing between procedures.

According to still another aspect of the present invention, the defibrillator preferably has eliminated some non-essential equipment that is commonly used with conventional internal defibrillators. Some of these items may include:

(1) Limiting the discharge energy to less than 50 Joules;
(2) Eliminating any ECG amplifiers;
(3) Eliminating any waveform or parametric display;

(4) Eliminating any waveform analysis or recording; and/or (5) Powering the device with reusable or disposable batteries.

The elimination of these items optimally allows for a compact, lightweight, internal cordless defibrillator that eliminates the need to keep a conventional defibrillator in the operating room beyond a safe point (due to the fact that the instrument is not sterile) and running long bulky cables to the paddles.

Figure 1:
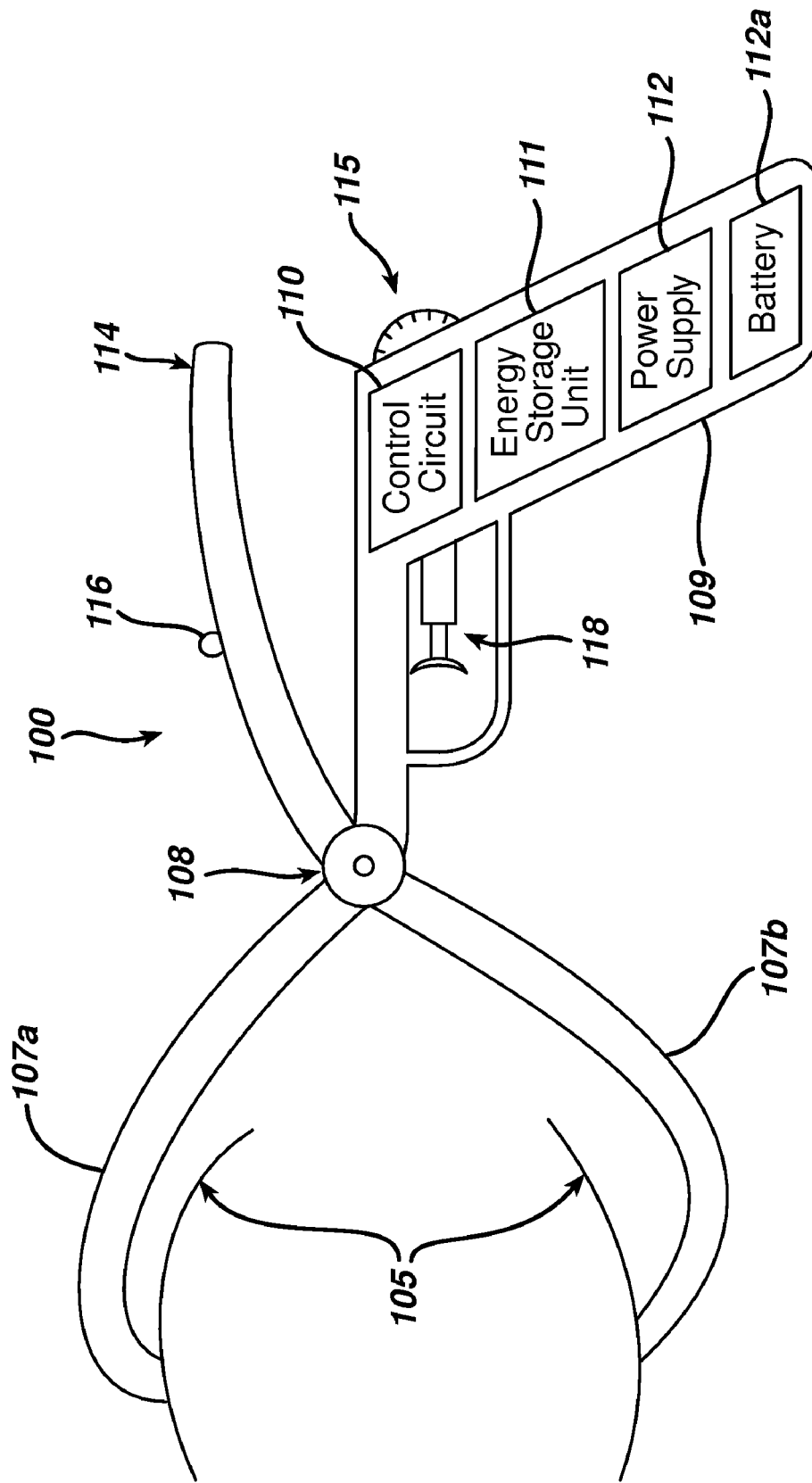
FIG. 1 illustrates a first aspect of the present invention, wherein a cordless internal defibrillator utilizes paddles that are controlled by a single handle.

FIG. 1 illustrates a first aspect of the present invention. This particular illustration is a "one-handed design" but it should be understood that a two-handed design may also be used. In either case the defibrillator circuitry is self-contained in the paddles or the handle. The internal defibrillator includes a pair of electrodes (105) that are adapted for internal application to the heart, i.e., to shock the heart when the chest cavity is open, such as during open-heart surgery. The electrodes (105) are arranged respectively at end portions of a pair of paddles (107a, 107b). At least one of the paddles (107a, b) is pivotable relative to the other via pivot (108) so that the distance between the electrodes (105) can be varied. As different patients may have different sized hearts (including children), the ability to adjust the spread of the paddles permits greater flexibility than does a stationary distance.

Attached to the pivot (108) is a handle (109) that can be similar in size and shape to the handles on other hand-held tools, such as a power drill, or even a handgun. Arranged inside the handle are a control circuit (110), an energy-storage facility (111), and a power supply (112). The handle (109) is also adapted to receive a battery by arranging positive and negative contacts in a battery compartment (112a). Power from the battery compartment (112a) is fed to the power supply (112), and in turn the power supply supplies the energy for logic of control circuit (110) and the energy-storage facility (111). Optionally, there can be a dial and/or selection control switches (115) that are used to provide different charge settings to the patient. There is also a discharge switch (118) which the user pulls or presses, similar to a trigger on a handgun, so as to administer the electrical impulse.

A regulator arm (114) is attached to at least one of the paddles via the pivot and is biased so that the electrodes (105) are a predetermined distance apart. It is preferable that a locking mechanism or spring (116) retains the regulator arm (114) at a desired position so as to lock-in a desired distance between the electrodes (105).

The regulator arm may comprise part of an end of one of the paddles, or it could be a separate piece of material that can be used to adjust the bias or leverage applied to at least one of the paddles, so as to cause it to move. Preferably, the handle is made of an insulating material, or at least has an insulating coating arranged thereon. The user pushes the regulator handle (114) either toward or away from the handle (109) to vary the distance between the electrodes, so that the present invention can be used with patients of different ages and sizes (from children through geriatrics). Finally, it should be noted that the defibrillator may have automatic features, wherein once activated the unit determines whether and to what extent the heart should be shocked.

Figure 2:
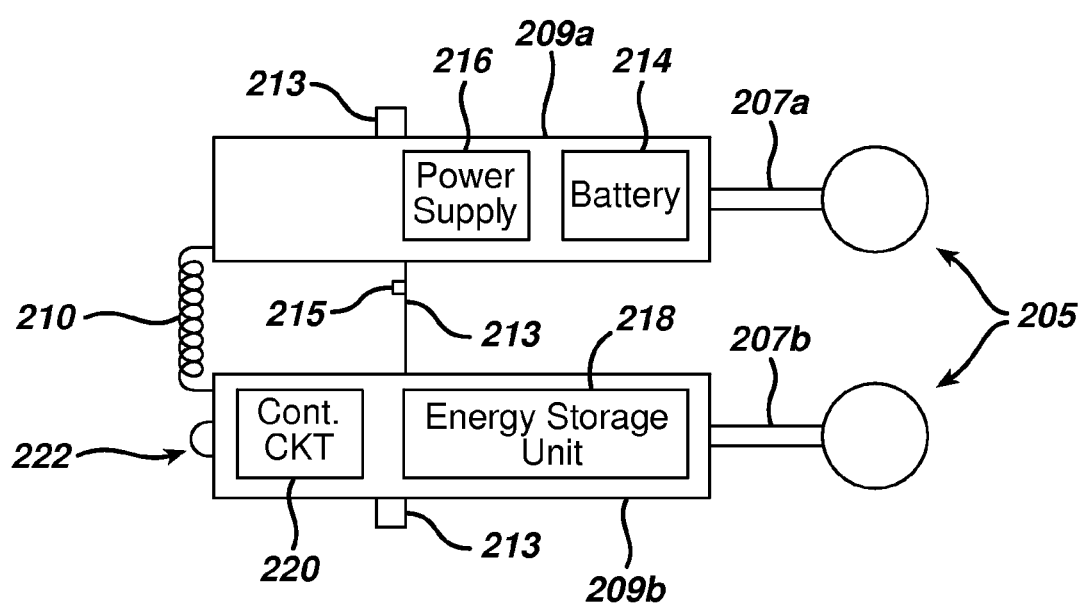
FIG. 2 illustrates a second aspect of the present invention, wherein a cordless internal defibrillator utilizes paddles that are controlled by two separate handles that can be separated or locked at a certain desired distance between the electrodes so as to operate as a single unit.

FIG. 2 illustrates a second embodiment of the present invention. This drawing shows an internal defibrillator with a dual-handle design, as opposed to the single-handle design shown in FIG. 1.

The electrodes (205) are respectively attached to one end a pair of paddles (207a, 207b). The paddles are connected to the respective left and right handles (209a, 209b). The left and right handles are electrically connected by at least one wire (210). It should be noted that any flexible conductor and/or flex board could provide a conduction path. Optionally, the handles (209a, 209b) can be arranged on a slidable track (213) which allows the electrodes (209a, 209b) to be spaced according to need. The track may have a locking mechanism (215) to hold the handles (and thus the electrodes) at the desired distance from each other. This locking mechanism could be a latch, or a wingnut and a bolt that can travel within a slot cut into the track, a hook, or any known type of lock device that a user can both lock and/or release quickly.

It should be noted that while the two-handle design contemplates one hand per handle, once the distance between the electrodes is locked at the track (213), only a single handle needs to be held, as the distance between the electrodes is fixed. Moreover, one could hold onto one of the handles and use the other hand to activate the shock to the patient after the device is arranged in proper position within the patient.

Arranged within the dual-handle design are the complete defibrillation circuitry, including a battery (214), a power supply (216), a storage unit (218), and a control circuit (220). It is contemplated that a battery would be arranged in the power-receiving unit. Optionally, there may also be a ready light (222) arranged on one of the handles to indicate when the defibrillator is ready for use. Similar to the controls (115) on the defibrillator shown in FIG. 1, the dual-handle design will also have a switch or knobs to control the amount and/or duration of the electrical impulse to be applied to the patient. The defibrillator may also have automatic features, wherein once activated the unit determines whether and to what extent the heart should be shocked.

In either embodiment of the present invention the arrangements provide a clutter-free defibrillator that allows easier use because of the lack of cables that are required by conventional internal defibrillators, improving the control of the unit, particularly the ability to maneuver the paddles into position. Several failure points are eliminated by arranging the circuitry within the handles/paddles. In the case of both a single handle and two-handle design, operator safety is improved as the internal defibrillator has no cables and is therefore tangle-free. Also, in both embodiments, some or all of the internal-defibrillator components can be used for a single patient and then thrown away. The disposability can eliminate the need to sterilize internal-defibrillator components, such as the paddle or electrodes, and thus reduce potential infection problems that could occur if, for example, the paddle is not sterilized properly.

Since the internal defibrillator is self-contained, yet another aspect of the invention can be to limit the discharge energy to less than 50 joules. While this energy discharge amount is optional, there will be a savings in size and power if such a limit is utilized. In addition, more power is saved and the unit can be made even lighter by eliminating items such as ECG amplifiers, the parametric display of a waveform or the analysis and/or recording of the waves. The device may be powered with reusable or disposable batteries.

A method of providing a single-handle internal defibrillator includes the steps of:

(a) attaching the pair of electrodes to first-end portions of the pair of paddles, respectively;

(b) connecting a second-end portion of the pair of paddles to a single handle, with at least one paddle of the pair of paddles being movable with respect to the other;

(c) providing an adjustment such as a regulator arm to adjust the movement so that the distance between the electrodes is variable; and, (d) arranging internal-defibrillator circuitry to be within the single handle.

Thus, the present invention eliminates the usage of large bulky cables that interfere with movement of the surgeons and nurses, reduces potential contamination issues by the need to arrange a defibrillator in a non-sterile field and then drape the cables back into the sterile field, reduces potential safety issues with the single-handle model, allows for setting the distance between the electrodes to permit more accurate placement of the electric shock, eliminates the need for two people to set up the defibrillator and cables, and eliminates the need for the general-purpose defibrillator in the operating room.

It should be understood that various modifications can be made by persons of ordinary skill in the art once they have gleaned the knowledge of the present invention, and such changes will lie within the spirit of the invention and the scope of the appended claims. For example, the shape of the electrodes, the shape of the paddles, the appearance of the single-handle and dual-handle may be changed in both size and shape. There can be, for example, other items in the defibrillation circuitry other than what is shown, so long as they are arranged within the handle of the device. The lock mechanism can be any known type of lock, so long as it serves the purpose of locking. Some or all of the components of the internal defibrillator may be disposable, for example, such as the paddle or just the electrodes, and the paddle may take any known shape according to need.

What is claimed is:

1. A single-handle internal defibrillator adapted to apply defibrillation electrodes directly to a heart in an open heart procedure, comprising:

a pair of paddles that includes a pair of electrodes respectively connected to first-end portions of the pair of paddles;

the pair of paddles coupled to a single-handle, with at least one paddle of the pair of paddles being adjustable in position with respect to the other paddle;

an adjustment mechanism, coupled to the single handle and to at least one of the paddles for adjusting the position of the electrode of at least one paddle with respect to the position of the electrode of the other paddle so that a distance between the electrodes is variable; and defibrillator circuitry coupled to the electrodes of the pair of paddles of the single-handle, further comprising a single discharge switch arranged at least partly within the single-handle, and wherein when the single discharge switch is actuatable by a same hand of an operator holding the single-handle which when actuated applies defibrillation energy to both paddles of the electrodes.

2. A single-handle internal defibrillator adapted to apply defibrillation electrodes directly to a heart in an open heart procedure, comprising:

a pair of paddles that includes a pair of electrodes respectively connected to first-end portions of the pair of paddles;

the pair of paddles coupled to a single-handle, with at least one paddle of the pair of paddles being adjustable in position with respect to the other paddle;

an adjustment mechanism, coupled to the single handle and to at least one of the paddles for adjusting the position of the electrode of at least one paddle with respect to the position of the electrode of the other paddle so that a distance between the electrodes is variable; and defibrillator circuitry coupled to the electrodes of the pair of paddles of the single-handle, wherein the defibrillator circuitry includes a control circuit in communication with a single discharge switch to initially request a shock to a patient, and further comprising the single discharge switch arranged at least partly within the single-handle, and wherein the single discharge switch is actuatable by a same hand of an operator holding the single-handle which when actuated applies defibrillation energy to both paddles of the electrodes.

3. A single-handle internal defibrillator adapted to apply defibrillation electrodes directly to a heart in an open heart procedure, comprising:

a pair of paddles that includes a pair of electrodes respectively connected to first-end portions of the pair of paddles;

the pair of paddles coupled to a single-handle, with at least one paddle of the pair of paddles being adjustable in position with respect to the other paddle;

an adjustment mechanism, coupled to the single handle and to at least one of the paddles for adjusting the position of the electrode of at least one paddle with respect to the position of the electrode of the other paddle so that a distance between the electrodes is variable; and defibrillator circuitry coupled to the electrodes of the pair of paddles of the single-handle, further comprising a control switch arranged at least partly within the single-handle that is adapted for a user to vary the amount, duration, and type of electrical impulse applied to a patient with a same hand of the user that is holding the single-handle.

4. A method of providing a single-handle defibrillator adapted to apply defibrillation electrodes directly to a heart, comprising the steps of:

(a) attaching a pair of electrodes respectively to a first-end portions of a pair of paddles;

(b) connecting the pair of paddles to a single handle, with at least one paddle of the pair of paddles being movable with respect to the other paddle and the single handle; and, (c) providing an adjustment mechanism to adjust the position of the electrode of at least one paddle with respect to the other electrode so that a distance between the electrodes is variable; and, (d) arranging defibrillator circuitry to be electrically coupled to the electrodes of the paddles of the single-handle by actuation of a single switch located in a single-handle and wherein the single discharge switch is actuatable by a same hand of an operator holding the single-handle.

5. The method according to claim 4, further comprising (e) providing a locking mechanism to keep the adjustment mechanism fixed at a desired position so as to lock-in a desired distance between the electrodes.

* * * * *